US00PP10452P

United States Patent [19]

Wain

[11] Patent Number: Plant 10,452

[45] Date of Patent: Jun. 16, 1998

[54] CHRYSANTHEMUM PLANT NAMED 'CLEAGAR SP1'

[75] Inventor: Peter Wain, Portsmouth, United Kingdom

[73] Assignee: Cleangro Limited, United Kingdom

[21] Appl. No.: 751,868

[22] Filed: Nov. 18, 1996

[51] Int. Cl.[6] ..... A01H 5/00

[52] U.S. Cl. ..... Plt./80

[58] Field of Search ..... Plt./76, 79, 80

[56] References Cited

U.S. PATENT DOCUMENTS

P.P. 1,932 4/1960 Boerner ..... Plt./82

OTHER PUBLICATIONS

UPOV-ROM, 1997/03, Plant Variety Database, "Sandpiper" excerpt.

*Primary Examiner*—Howard J. Locker

*Attorney, Agent, or Firm*—Christie, Parker & Hale L.L.P.

[57] ABSTRACT

A distinct cultivar of Chrysanthemum plant named Cleagar sp1, characterized by its mounded compact plant habit and slow growth rate; decorative-type inflorescences; soft coral ray florets that become lighter coral pink with development; numerous ray florets per inflorescence; and good garden performance.

2 Drawing Sheets

1

The present invention relates to a new and distinct cultivar of garden Chrysanthemum plant, botanically known as *Dendranthema grandiflora* and referred to by the cultivar name Cleagar sp1.

The new cultivar is a product of a planned breeding program conducted by the inventor in Chichester, West Sussex, United Kingdom. The objective of the breeding program was to create new garden Chrysanthemum cultivars having desirable inflorescence colors and good garden performance.

The new cultivar originated from a cross made by the inventor of the commercial cultivar Grenadine (U.S. Plant Pat. No. 5,338) as the female, or seed, parent with the proprietary selection 10/GM/94 as the male, or pollen, parent.

The new Chrysanthemum was discovered and selected by the inventor as a flowering plant within the progeny of the stated cross in a controlled environment in Chichester, West Sussex, United Kingdom.

Asexual reproduction of the new cultivar by terminal cuttings taken at Chichester, West Sussex, United Kingdom, has shown that the unique features of this new Chrysanthemum are stable and reproduced true to type in successive generations.

The following traits have been repeatedly observed and are determined to be the unique characteristics of Cleagar sp1. These characteristics in combination distinguish Cleagar sp1 as a new and distinct cultivar:

1. Mounded compact plant habit and slow growth rate.
2. Decorative-type inflorescences.
3. Soft coral ray florets that become lighter coral pink with development.
4. Numerous ray florets per inflorescence.
5. Good garden performance.

The cultivar Cleagar sp1 has not been observed under all possible environmental conditions. The phenotype may vary somewhat with variations in environment such as temperature, daylength and light intensity, without, however, any variance in genotype.

In side-by-side comparisons in Chichester, West Sussex, United Kingdom, under commercial practice, plants of the new Chrysanthemum are shorter, slower in growth rate, have smaller inflorescences and flower later than plants of the female parent, the cultivar Grenadine. In addition, ray florets

2 of plants of the new Chrysanthemum are lighter in color than ray florets of plants of the cultivar Grenadine. In the same comparisons, plants of the new Chrysanthemum have more ray florets than plants of the male parent, the proprietary selection 10/GM/94. In addition, plants of the new Chrysanthemum have coral ray florets and decorative-type inflorescences whereas plants of the proprietary selection 10/GM/94 have yellow ray florets and daisy-type inflorescences.

The accompanying colored photographs illustrate the overall appearance of the new cultivar, showing the colors as true as it is reasonably possible to obtain in colored reproductions of this type. The first photograph comprises a side perspective view of a typical flowering 16.5-cm container of Cleagar sp1 with one cutting in the container. The second photograph comprises a close-up view of five leaves at different stages of development and a fully opened inflorescence. Foliage and floret colors in the photographs may appear different from the actual colors due to light reflectance.

In the following description, color references are made to The Royal Horticultural Society Colour Chart except where general terms of ordinary dictionary significance are used. The following observations and measurements describe plants grown in Oxnard, Calif., under commercial practice in a glass-covered greenhouse with average night temperatures of 18C, average day temperatures of 30C, and light levels of 2,000 (cloudy conditions) to 9,000 (sunny conditions) footcandles.

After sticking unrooted cuttings of the new cultivar, plants received 4 weeks of long day/short nights followed by short day/long nights until flowering. Measurements and numerical values represent ranges or averages for six typical flowering plants.

Botanical classification: *Dendranthema grandiflora* cultivar Cleagar sp1.

Commercial Classification: Garden Chrysanthemum.

Parentage:

*Female, or seed, parent.*—*Dendranthema grandiflora* commercial cultivar Grenadine (U.S. Plant Pat. No. 5,338).

*Male, or pollen, parent.*—*Dendranthema grandiflora* proprietary selection 10/GM/94.

Propagation:

*Type.*—Terminal tip cuttings.

*Time to rooting.*—10 to 12 days with soil temperatures of 20C.

*Rooting habit.*—Fine, fibrous and well-branched.

Plant description:

*Appearance.*—Perennial herbaceous garden plant. Mounded and compact growth habit. Moderately vigorous but slow growth rate.

*Plant height.*—About 18 cm.

*Lateral branch length.*—About 15 cm.

*Quantity of lateral branches after removal of apical meristem.*—About 3.

*Stem color.*—138B.

*Foliage description.*—Number of leaves per plant: About 48. Number of leaves per lateral branch: About 16. Leaf arrangement: Alternate. Leaf size, fully expanded: Length: About 4.2 cm. Width: About 4 cm. Leaf apex: Apiculate. Leaf base: Attenuate. Leaf margin: Palmately lobed. Leaf texture: Abaxial and adaxial surfaces slightly pubescent, smooth and dull. Veins prominent on abaxial surface. Petiole length: About 1.8 cm. Color: Young foliage adaxial surface: 146A. Young foliage abaxial surface: 146B. Fully expanded foliage adaxial surface: 147A. Fully expanded foliage abaxial surface: 147B. Venation adaxial surface: 147C. Venation abaxial surface: 147B. Petiole: 147C.

Inflorescence Description:

*Appearance.*—Decorative-type inflorescence form. Inflorescences borne on terminals above foliage, arising from leaf axils. Disc and ray florets arranged acropetally on a flat capitulum.

*Flowering response.*—Under natural conditions, plants flower in the autumn. Inflorescence initiation and development can be induced under short day/long night conditions (at least 13.5 hours of darkness). Plants exposed to 3 or 4 weeks of long day/short night conditions after sticking followed by photoinductive short day/long night conditions, flower about 54 days later.

*Quantity of inflorescences.*—About 6 inflorescences per flowering stem.

*Inflorescence size.*—Diameter: About 4 cm. Depth (height): About 1.5 cm. Diameter of disc: About 5 mm.

*Opening inflorescences.*—Bud shape: Spherical. Bud size: Length: About 6 mm. Width: About 7 mm. Bud color: 29D.

*Ray florets.*—Shape: Spatulate, broad tipped spoon with tubular base. Size: Length: About 2 cm. Width: About 7 mm. Apex: Rounded, tri-dentate. Base: Acute, tubular. Margin: Entire. Texture: Ridged, smooth and glabrous. Aspect: Flat. Number of ray florets per inflorescence: About 126. Color: When opening, adaxial surface: 37B. When opening, abaxial surface: 23D. Mature, adaxial surface: 36A. Mature, abaxial surface: 23D. Fading to: 27A.

*Disc florets.*—Shape: Tubular. Size: Length: About 4 mm. Width: About 1 mm. Number of disc florets per inflorescence: About 24. Color: Immature: 154D. Mature: 154C.

*Peduncle.*—Aspect: Strong and angled about 35° to the stem. Length: First peduncle: About 3.8 cm. Fourth peduncle: About 5.5 cm. Texture: Pubescent. Color: 146C.

*Reproductive organs.*—Androecium: Present on disc florets only. Anther color: 14A. Pollen: Moderate, 14A in color. Gynoecium: Present on both ray and disc florets. Style color: 154C.

Disease resistance: Under commercial greenhouse and garden conditions, plants of the new Chrysanthemum have not demonstrated resistance, tolerance nor susceptibility to diseases common to Chrysanthemums.

Seed production: Seed production has not been observed.

It is claimed:

1. A new and distinct cultivar of Chrysanthemum plant named Cleagar sp1, as illustrated and described.

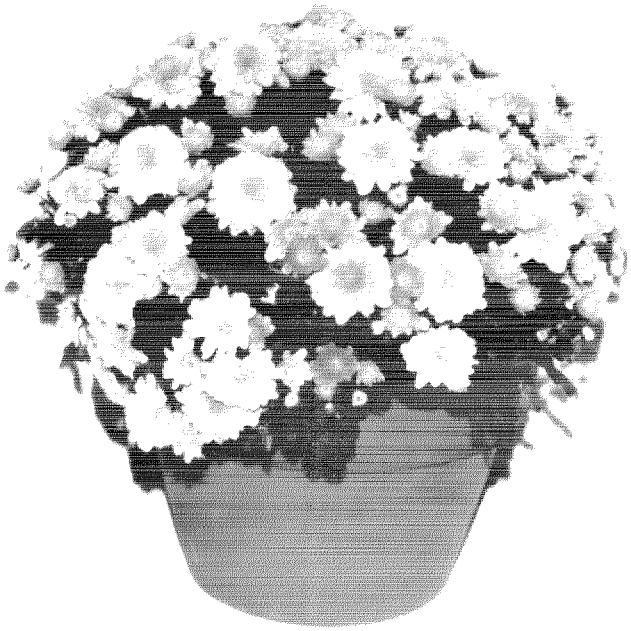

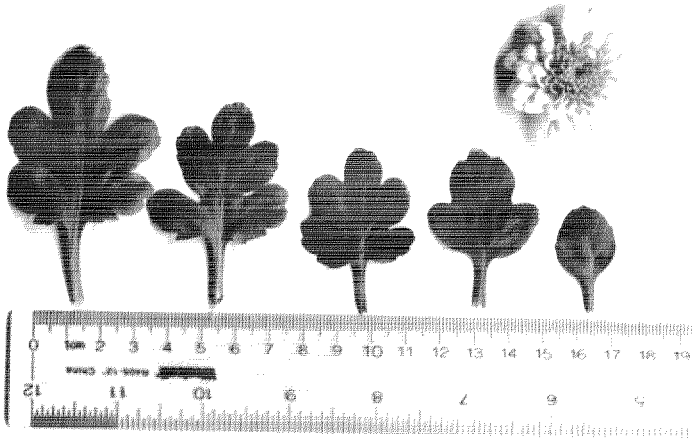

* * * * *